US 8,753,616 B2

(12) United States Patent
Hullmann et al.

(10) Patent No.: US 8,753,616 B2
(45) Date of Patent: Jun. 17, 2014

(54) PROCESS FOR PERMANENT SHAPING OF HUMAN HAIR

(75) Inventors: Alexandra Hullmann, Egelsbach (DE); Jonathan Wood, Weinheim (GB); Frank Kufner, Darmstadt (DE); Sabine Schafer, Rüsselsheim (DE); Bernd Nocker, OberRamstadt (DE)

(73) Assignee: KAO Germany GmbH, Darmstadt (DE)

( * ) Notice: Subject to any disclaimer, the term of this patent is extended or adjusted under 35 U.S.C. 154(b) by 56 days.

(21) Appl. No.: 13/512,790

(22) PCT Filed: Dec. 3, 2010

(86) PCT No.: PCT/EP2010/007345
§ 371 (c)(1),
(2), (4) Date: May 30, 2012

(87) PCT Pub. No.: WO2011/069619
PCT Pub. Date: Jun. 16, 2011

(65) Prior Publication Data
US 2012/0234339 A1      Sep. 20, 2012

(30) Foreign Application Priority Data
Dec. 9, 2009 (EP) .................................. 09015229

(51) Int. Cl.
*A61Q 5/04* (2006.01)

(52) U.S. Cl.
USPC ........ 424/70.6; 424/70.2; 424/70.5; 132/203; 132/205

(58) Field of Classification Search
None
See application file for complete search history.

(56) References Cited

U.S. PATENT DOCUMENTS

| 4,214,596 A | 7/1980 | Davis et al. |
| 5,655,552 A * | 8/1997 | Samain .......................... 132/205 |
| 7,824,664 B2 * | 11/2010 | Devin-Baudoin ......... 424/70.12 |
| 2008/0142033 A1 * | 6/2008 | Sabbagh et al. ............... 132/204 |

FOREIGN PATENT DOCUMENTS

| EP | 0 116 838 A2 | 8/1984 |
| EP | 1 920 755 A1 | 5/2008 |
| GB | 1 453 527 A | 10/1976 |
| WO | 2005/018587 A1 | 3/2005 |

OTHER PUBLICATIONS

International Search Report Dated Apr. 7, 2011, Mailed Apr. 19, 2011.

* cited by examiner

*Primary Examiner* — Jyothsna Venkat
(74) *Attorney, Agent, or Firm* — Norris McLaughlin & Marcus PA

(57) ABSTRACT

The present invention concerns a process for permanent shaping of human hair used both for the permanent waving of human hair with an excellent waving effect as well as for the straightening of curled hair. Accordingly, the first object of the present invention is a process for permanent shaping hair wherein an aqueous composition comprising at least one inorganic salt is applied onto hair and optionally processed up to 20 min and optionally rinsed off and subsequently a composition comprising at least one reducing agent is applied and rinsed off from hair after a processing time of 1 to 30 min and at a temperature of 20 to 45° C. and a composition comprising at least one oxidizing agent is applied and processed for 1 to 20 min at a temperature range of 20 to 45° C. and rinsed off from hair.

8 Claims, No Drawings

PROCESS FOR PERMANENT SHAPING OF HUMAN HAIR

This application is a 371 application of PCT/EP2010/007345 filed Dec. 3, 2010, which claims foreign priority benefit under 35 U.S.C. §119 of European Application No. 09015229.9 filed Dec. 9, 2009.

The present invention concerns a process for permanent shaping of human hair used both for the permanent waving of human hair with an excellent waving effect as well as for the straightening of curled hair.

It is generally known that permanent shaping is carried out according to a two step process. In the first step, the reductive splitting of the cysteine disulfide bonds is achieved by a reducing agent, and in the second step, neutralization is carried out by application of an oxidizing agent, whereby the cysteine disulfide bonds are restored in the new shape.

The reducing agent still most frequently used today is thioglycolic acid, also in form of the salts thereof, in particular its ammonium salt, although numerous other thio compounds have been proposed for this purpose, which, however, mostly did not succeed.

The compositions containing thioglycolates are customarily applied at a pH-value between 7 and 10, in particular 8.5 and 9.5.

It is also well known in the art that use of an intermediate treatment is advantageous in order to realize more efficient perming and reduce hair damage. These compositions usually comprise only salts at higher concentration in order to de-swell hair which occurs usually when hair is treated with strong alkaline compositions especially in the presence of a reducing agent. Although the prior art has quite developed, there is still need for further improvements, especially in realizing lower hair damage without loss of perming and/or straightening efficiency.

The present invention starts from the task of providing a process for the permanent shaping of human hair wherein an aqueous composition is applied onto hair prior to application of reducing composition which delivers excellent waving and straightening performance. Hair waved or straightened according to the process of the present invention looks attractive and feels natural upon touching by hand.

Accordingly, the first object of the present invention is a process for permanent shaping hair wherein an aqueous composition comprising at least one inorganic salt is applied onto hair and optionally processed up to 20 min and optionally rinsed off and subsequently a composition comprising at least one reducing agent is applied and rinsed off from hair after a processing time of 1 to 30 min and at a temperature of 20 to 45° C. and a composition comprising at least one oxidizing agent is applied and processed for 1 to 20 min at a temperature range of 20 to 45° C. and rinsed off from hair.

In a further preferred form of the invention, the hair is washed and more preferably shampooed prior to application of the aqueous composition comprising at least one inorganic salt.

In case that the aim of using the process is perming (curling), prior to application of the reducing agent or during the application of the reducing agent, even after the application of the reducing agent, hair is put on the curlers and the curlers are taken out prior to or during or after application of the oxidizing composition or after processing of the oxidizing composition. The selection of the timing when the curlers are put and taken off from hair is very much dependent on the curling efficiency aimed. For stronger curls it is preferred that the curlers are put on the hair before application of the reducing agent. Putting curlers onto hair during or after the application of the reducing agent produces relatively weaker curls. For stronger curls it is preferred that the curlers are taken off at the end of the processing time of oxidizing agent, and for relatively weaker, slight curling effect, curlers are taken off before application of the oxidizing agent or the latest right after application of the oxidizing agent.

According to the novel process of the present invention, an aqueous composition comprising at least one inorganic salt is applied onto keratin fibers prior to application of the reducing agent. In principal any water soluble salt is suitable for the purpose of the present invention. In the preferred embodiment, salts are preferably selected from salts of mono or divalent cations with mono and divalent anions. Preferred cations are sodium, calcium, potassium and magnesium and anions are chloride and sulfate. Suitable ones are such as sodium chloride, sodium sulfate, magnesium sulfate, potassium chloride, potassium sulfate, magnesium chloride, calcium chloride, ammonium salts such as ammonium chloride and ammonium sulfate. Additionally it has been found to be suitable especially salts of iodide ions especially potassium and sodium slats, copper chloride, cupper sulphate, cobalt chloride, cerium sulphate, cerium chloride, vanadium sulphate, lithium chloride, potassium dichromate, magnesium acetate, calcium nitrate, barium nitrate, magnesium oxide, and ammonium nitrate. Preferred inorganic salts are sodium chloride, sodium sulfate, magnesium sulfate, potassium chloride, potassium sulfate, magnesium chloride, calcium chloride and salts of iodide ions. More preferably the salts are sodium chloride, sodium sulfate, magnesium sulfate, potassium chloride, potassium sulfate, magnesium chloride and salts of iodide ions especially potassium and sodium salts. In particular, with magnesium sulfate, sodium chloride and potassium iodide exceptionally good results were observed.

Concentration of at least one inorganic salt in the aqueous composition is typically from 0.01 to 20%, preferably 0.05 to 15% and most preferably 0.1 to 10% and in particular 0.2 to 7.5% by weight calculated to the total composition. The concentration range disclose herein is the total concentration of the inorganic salts in case more then one is used in mixture.

In a preferred embodiment, aqueous composition comprising at least one inorganic salt is processed up to 20 min, preferably up to 15 min and more preferably up to 10 min with or without using heat, preferably at a temperature range between 20 and 45° C., on hair prior to application of reducing composition.

It is possible to prepare the aqueous composition comprising at least one inorganic salt immediately before application onto hair by adding inorganic salt into appropriate aqueous base and/or composition comprising additional cosmetic ingredients (see below).

As a rule, an aqueous composition comprising only one inorganic salt is basically appropriate for achieving intensive and homogeneous colorations. It must be noted that aqueous compositions may also comprise two or more inorganic salts. Further additives may be used in order to achieve further effects such as enhancing combability, shine etc. or in order to make application onto hair easier such as thickening agents for adjusting the consistency.

The aqueous composition of inorganic salts can be thickened with polymers of any kind, namely, anionic, cationic, nonionic and/or amphoteric polymers. Natural polymers such as chitosan and its derivatives, cellulose and its derivatives and especially hydroxyethylcellulose, guar gum and its derivatives serve excellently for this purpose. The viscosity values targeted should not be very high in any case should not be more than 2000 mPa·s measuered with either Höppler or Brookfield viscosimeter with the known means as explained in the manuals of the respective equipments at 20° C.

Aqueous composition of inorganic salt may comprise cationic polymers as thickeners and at the same time conditioning agents which enhances first of all combability and therefore makes applications onto hair easier. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, those cationic polymers known with their CTFA category name Polyquaternium may as well be added into pre-treatment compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7, It is also possible to use mixtures of various cationic polymers.

The cationic polymers also include the quaternized products of graft polymers from organopolysiloxanes and polyethyl oxazolines described in EP-A 524 612 and EP-A 640 643.

According to the present invention total concentration of polymers of anionic, cationic, non-ionic and/or amphoteric or zwitterionic character is in the range of 0.05-10%, preferably 0.1-7.5%, preferably 0.2-7.5% and most preferably 0.2-5% by weight, calculated to the total composition.

The aqueous composition of inorganic salt can comprise additionally one or more surfactants selected from non-ionic, anionic, cationic and amphoteric ones.

The surfactants suitable for the compositions according to the invention are first of all those nonionic surfactants. Pretreatment compositions according to the invention comprise one or more nonionic surfactants. Preferred nonionic surfactants are ethoxylated fatty alcohols according to the following formula:

$$R_1(CH_2CH_2O)_nH$$

where $R_1$ is a saturated or unsaturated, linear or branched alkyl chain with 12 to 22 C atoms and n is a number between 2 and 50 preferably 2 to 40, more preferably 2 to 30. In one of the prefreed embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. "Ceteareth-20", Steareth-2, Further nonionic surfactants suitable as emulsifiers in hair treatment compositions according to the invention are those polyethylene glycol ethers of monogylcerides according to the general formula

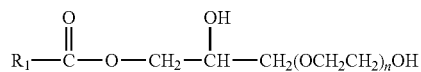

$R_1$ and n are same as above. Examples to those types of nonionic surfactants are PEG-7-glyceryl cocoate known with the trade name Cetiol HE from Cognis, PEG-8-glyceryl laurate know with the trade name Glycerox L8 from Croda Chemicals, PEG-10 glyceryl oleate, PEG-15 glycerryl isostearate, PEG-5 glycerryl stearate, PEG-15 gylceryl ricinoleate, etc.

Further nonionic surfactants suitable for treatment compositions according to the invention are alkyl polyglucosides of the general formula

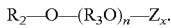

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Nonionic surfactant components are, for example, long-chain fatty acid mono- and dialkanolamides, such as coco fatty acid monoethanolamide and myristic fatty acid monoethanolamide, which can also be used as emulsifiers according to the invention.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain, Those are on the market, for example, under the trade names "Ammonyx®", "Aromox®" or "Genaminox®".

Anionic surfactants of the sulfate, sulfonate, carboxylate types are as well suitable in the pre-treatment composition of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

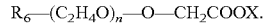

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

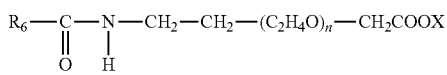

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, the compositions according to the invention can also contain amphoteric or zwitterionic surfactants as emulsifiers.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

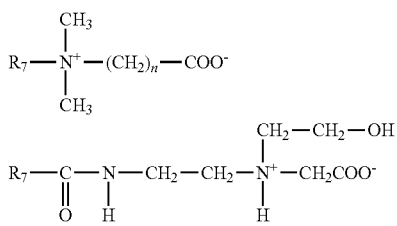

wherein $R_7$ is a $C_8$-$C_{18}$-alkyl group and n is 1 to 3; sulfobetaines of the structure

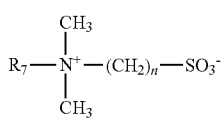

wherein $R_7$ and n are same as above;
and amidoalkyl betaines of the structure

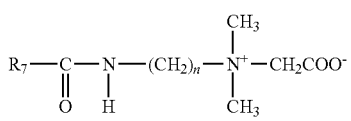

wherein $R_7$ and n are same as above.

Cationic surfactants are useful in the aqueous composition comprising at least one inorganic salt as well and particularly as conditioning agent and according to the general formula

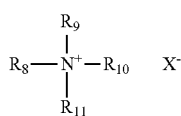

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4, and
$R_9$ is a hydrogen, lower alkyl chain with 1 to 4 carbon atoms, saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4, and
$R_{10}$ and $R_{11}$ are independent from each other H or lower alkyl chain with 1 to 4 carbon atoms, and X is chloride, bromide or methosulfate.

Suitable cationic surfactants and or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®".

Again from the above quaternary ammonium compounds disclosed with the general formula, especially preferred as conditioning ingredient are these compounds are known per se and on the market, for example, under the trade name "INCROQUAT® HO" or "OCS". Those compounds are known with a general ingredient category under "amidoquat" in the cosmetic industry.

According to present invention total concentration of surfactants of anionic, cationic, non-ionic and/or amphoteric or zwitterionic character is in the range of 0.05-10%, preferably 0.05-7.5% and most preferably 0.05-5% by weight, calculated to the total composition.

Aqueous composition of at least one inorganic salt can also comprise other conditioning agents selected from oily substances and nonionic substances. Oily substances are selected from such as silicone oils volatile or non-volatile, natural and synthetic oils. Among silicone oils those can be added include dimethicone, dimethiconol, polydimethylsiloxane, DC fluid ranges from Dow Corning, arylated silicones, aminated silicones, natural oils such as olive oil, almond oil, avocado oil, weizenkeim oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Conditioners mentioned above can be contained at a concentration of below 1%, preferably below 0.75% by weight, calculated to total composition.

The aqueous composition comprising at least one inorganic salt can contain one or more organic solvent. Examples are such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of one or more organic solvents is in the range of 1 to 25%, preferably 1 to 20%, more preferably 1 to 15% and most preferably 1 to 10% by weight, calculated to the total composition.

Application of the aqueous composition can be done in any form which enables effectively and homogeneously bringing the compositions onto hair. Aqueous composition can be packed into a bottle with a nozzle, which enables easy application, or with a spray device (pump spray) or with a pump, which enables dispensing the composition in the form of liquid or foam (pump foamer). Composition may also be offered in an aerosol bottle from which the composition is dispensed as foam. In the aerosol form, dispensing as a spray may also find its applications in the daily practice. In the case that aerosol form is preferred, suitable propellant gas or mixtures must be added to the composition to make dispensing in the preferred form possible.

In principal pH of the aqueous composition comprising at least one inorganic salt is not critical. However, preferably the pH of the composition must be chosen in a range which does not make any big changes in the pH of the reducing composition applied subsequently. Preferably the pH of the aqueous composition is in the range of 4 to 9, more preferably 5 to 8.5 and most preferably 6 to 8.

The reducing composition comprises at least one reducing compound. Preferred are thioglycolic acid and thiolactic acid as well as the salts thereof, in particular the ammonium and ethanolamine salts. Further useful thio compounds are in particular cysteine or the hydrochloride thereof, homocysteine, cysteamine, N-acetyl cysteine, thioglycerol, ethanediol monothioglycolate, 1,2-propyleneglycol monothioglycolate (see also WO-A 93/1791), 1,3-propanediol monothioglycolate or the isomer mixture resulting therefrom, 1,3-butanediol and 1,4-butanediol monothioglycolate and the isomer mixtures therefrom, polyethylene glycol, such as di-, tri- and tetraethyleneglycol monothioglycolates, glycerol monothiolactate and further thio acids and the esters thereof, as well as mixtures thereof.

The use of inorganic reducing sulfur compounds such as sodium hydrogen sulfite is basically also possible.

The total reduction agent content in the compositions according to the invention customarily amounts from 0.5% to 15%, preferably 1 to 15%, more preferably 2 to 12.5% and most preferably 2.5 to 12.5% by weight, calculated to total composition.

The composition comprising reducing agents can, if necessary, comprise alkalizing agents. Their quantity is dependent on the reducing agent and the desired pH-value of the composition. Reducing agent compositions preferably contain about 0.1% to about 5%, in particular about 0.5% to about 2.5% by weight thereof, calculated to the total composition. Alkalizing agents preferred within the scope of the invention are ammonium carbamate, ammonia and/or ammonium(bi)carbonate, triethanolamine and monoethanolamine. It is desirable to adjust the pH-value between about 6.5 and 10.5, preferably about 7 to 9.5.

The viscosity best suited for the reducing compositions proved to be in the range of about 500 to 10,000 mPa·s, preferably about 1,000 to about 5,000 mPa·s, measured at 20° C. in a Brookfield viscosimeter (no. 5 spindle), whereas the viscosity suited for the straightening compositions is preferably higher in a range up to about 50,000 mPa·s, preferably up to 30,000 mPa·s measured at 20° C. in a Brookfield viscosimeter (no. 5 spindle).

The viscosity is adjusted by addition of the appropriate amounts of thickening agents known per se and as mentioned above, such as cellulose derivatives. Thickening may as well be realised by formulating a composition in form of an emulsion with the use of $C_{10}$-$C_{22}$-fatty alcohols, in admixture with long mono alkyl chain quaternary ammonium surfactants.

The third component used in the inventive process is a composition comprising at least one oxidizing agent. Suitable ones are such as hydrogen peroxide and sodium bromate. Most preferred is hydrogen peroxide. Oxidizing agent is comprised at a concentration of 0.05 to 15%, preferably 0.1 to 15% more preferably 0.25 to 12.5% and most preferably 0.5 to 10% by weight calculated to total composition. The oxidizing composition has a pH between 2 and 7, preferably 2.5 and 6 and more preferably 3 and 5.

In a further preferred embodiment of the present invention, the inventive process preferably comprises application of an intermediate treatment after rinsing off the reducing composition and prior to application of the oxidizing composition.

Intermediate composition used in the inventive process of the present invention comprises further at least one salt, preferably at a concentration of 0.5 to 15%, more preferably 1 to 12.5% and most preferably 2 to 12.5% by weight calculated to total composition. The suitable salts are the same ones as mentioned above for the aqueous composition applied prior to reducing step. Most preferred are again the same ones mentioned above.

Intermediate treatment composition comprises preferably at least one oxidizing agent at a concentration of 0.1 to 5%, preferably 0.2 to 5% more preferably 0.2 to 3% and most preferably 0.2 to 2% by weight calculated to total composition. Suitable oxidizing agents are such as hydrogen peroxide and sodium bromate. Most preferred is hydrogen peroxide.

The intermediate treatment composition has a pH between 2 and 7, preferably 2.5 and 6 and more preferably 3 and 5.

Further, according to a further preferred embodiment, intermediate treatment compositions comprise at least one cationic surfactant disclosed above in the range from 0.05% to 5%, preferably 0.1% to 2.5%, more preferably 0.2 to 2% by weight, calculated to total of intermediate treatment composition. Suitable ones are as mentioned above.

Any of the compositions used in the inventive process of the present invention can comprise one or more of the following ingredients.

One or more of the compositions may comprise at least one ubiqinone of the formula

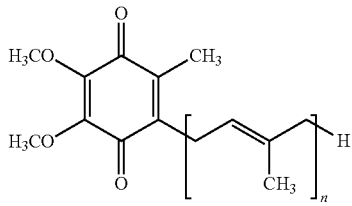

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of each composition.

The compositions comprise ubichinone which is preferably selected from the ones where n is a number between 6 and 10 and more preferably it is ubichinone 50 where n is 10, also known as Coenzyme Q10.

Although mentioned above for the aqueous composition used in the first step, the other compositions may also comprise one or more surfactants selected from anionic, nonionic, cationic and amphoteric ones. Their proportion ranges from about 0.05% to about 10%, in particular from about 0.1% to about 5% by weight, calculated to total of each composition. The suitable ones are mentioned above for each category of surfactants.

Cationic polymers and organic solvents may be comprise in any compositions used in the process of the present invention, unless otherwise mentioned.

Composition can also comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition of the present invention can comprise further ceramide type of compound with the general formula

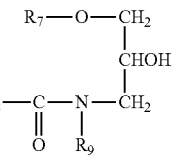

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of $C_{10}$ to $C_{22}$ may be incorporated into the compositions of the present invention at a concentration of preferably 0.01 to 2.5% by weight calculated to total of each composition.

In a further preferred embodiment of the present invention, intermediate treatment composition comprises at least one diamine compound. Preferred diamide compounds are according to the general structure

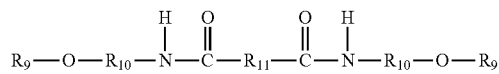

wherein $R_9$ is a linear or branched, saturated or unsaturated alkyl chain with 1 to 12 C atoms which may be substituted with hydroxy and/or alkoxy groups, preferably $R_9$ is linear or branched, saturated or unsaturated alkyl chain with 1 to 12 C atoms which may be substituted by 1 to 3 substituents selected from a hydroxy group and C1 to C6 alkoxy group, more preferably $R_9$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{10}$ is linear or branched alkyl chain with 1 to 5 C atoms, preferably linear or branched alkyl chain with 2 to 5 C atoms and more preferably an alkyl chain with 2 to 3 C atoms, and $R_{11}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

(A)

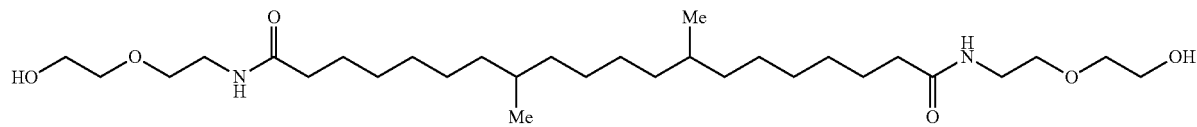

(B)

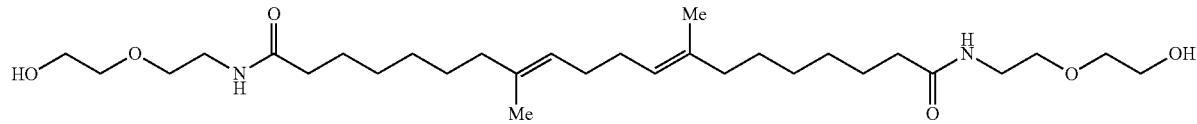

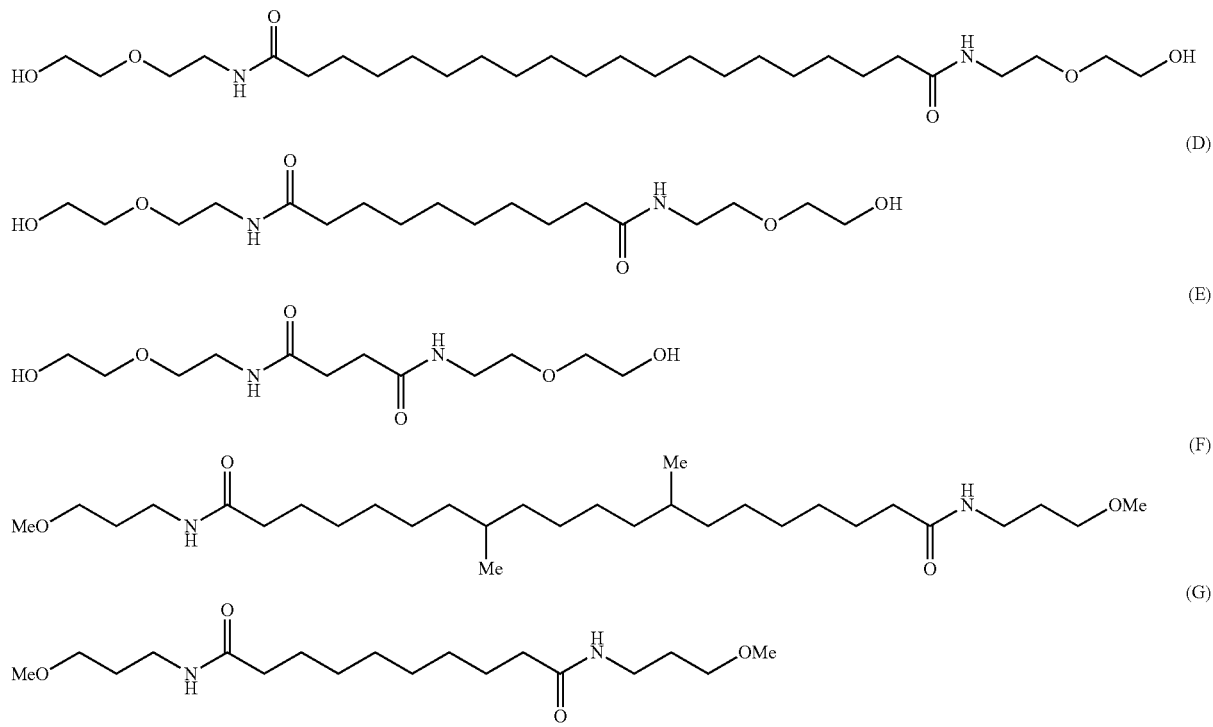

Particularly preferred diamide compound is the compound F which is bis (methoxypropylamido) isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to total of each composition.

Another preferred compound in the permanent shaping composition of the present invention is silicone compounds and especially aminated silicones such as amodimethicone available from for example Dow Corning under the brand names Dow Corning 949 Emulsion and Dow Corning 2-8194 ME. Concentration of silicones, especially amodimethicone, is in the range of 0.05 to 2.5%, preferably 0.1 to 1% by weight calculated to total or each composition.

Additionally, one or more natural oil component may be incorporated into the compositions of the present invention. Suitable are such as olive oil, almond oil, avocado oil, wheatgerm oil, ricinus oil or their mixture. Concentration of these natural oil ingredients should be 0.01 to 2.5%, preferably 0.01 to 1%, more preferably 0.05 to 0.5% by weight, calculated to total each composition.

The compositions used according to the invention can naturally comprise all the substances customarily found in permanent shaping compositions, a list of which will not be given here, and are preferably present as solutions, gels with a higher or lower viscosity, emulsions or creams. They can be single-phase products or compositions packed into separate packaging which are united upon application, as they are disclosed, for example, in DE-C 43 04 828.

In order to avoid repetition, reference is here made to the state of the art as it is described, for example, in "Ullmann's Encyclopedia of Industrial Chemistry", Vol. A12 (1986), pages 588 to 591, and in particular to the monography of K. Schrader, "Grundlagen and Rezepturen der Kosmetika", $2^{nd}$. Ed. (1989, Hüthig Buchverlag) pages 823 to 840, as well as the article by D. Hollenberg et. al. in "Seifen-Öle-Fette-Wachse", 117 (1991), pages 81 to 87.

The compositions used in the inventive process of the present invention are preferably provided in a kit. Accordingly further objective of the present invention is a kit for permanent shaping keratin fibers preferably hair comprising a—an aqueous composition comprising at least one organic salt,
b—an aqueous composition comprising at least one reducing agent,
c—an aqueous composition comprising at least one oxidizing agent, and
d—optionally, another aqueous composition comprising at least one inorganic salt.

The following examples are to illustrate the invention, but not to limit it.

EXAMPLE 1

First Aqueous Composition

|  | % by weight |
|---|---|
| Potassium iodide | 0.5 |
| Hydroxyethylcellulose | 0.5 |
| Monoethanolamine | 4.8 |
| Hydrochloric acid | 4.0 |
| Water | q.s. to 100 |

Alkaline Permanent Wave for Normal Hair

|  | % by weight |
| --- | --- |
| Ammonium thioglycolate (60%) | 21.3 |
| Ammonium hydrogen carbonate | 5.0 |
| 1,3-butylene gylcol | 3.0 |
| Amodimethicone | 0.2 |
| PEG-40-Hydrogenated castor oil | 0.7 |
| Polyquaternium-7 | 0.5 |
| Perfume | 0.4 |
| Ammonia, 25% | ad pH 8.3 |
| Water | ad 100.0 |

Oxidizing Composition

|  | % by weight |
| --- | --- |
| Hydrogen peroxide | 2 |
| Phosphoric acid | q.s. to pH 3.5 |
| Water | to 100 |

With these compositions the hair was permanently waved according to the process of claim 1. Therefore, hair was shampooed and towel dried and the first aqueous composition was applied onto hair and processed for 10 min at ambient temperature and without rinsing off the composition, hair was put on curlers and reducing composition given above was applied onto hair and processed for about 15 minutes, rinsed off from hair and oxidizing composition was applied and processed for about 10 minutes and rinsed off from hair and curlers were taken off from hair. Homogeneous wave appearance and natural feeling hair was obtained. Exclusion of the first step resulted in less homogeneous perm appearance and especially natural hair feeling was lost.

EXAMPLE 2

Intermediate Composition

|  | % by weight |
| --- | --- |
| Coenzyme Q10 | 0.2 |
| Polysorbate-80 | 0.2 |
| Magnesium sulfate | 10 |
| Hydrogen peroxide | 2.5 |
| Cetrimonium chloride | 0.5 |
| Citric acid | q.s. to pH 4.2 |
| Water | q.s. to 100 |

The three compositions used in Example 1 were used in this example. The permanent shaping was carried out as follows:
Hair was shampooed and towel dried and the first aqueous composition was applied onto hair and processed for 5 min at ambient temperature and without rinsing off, hair was put on curlers and reducing composition given above was applied onto hair and processed for about 15 minutes, rinsed off from hair and the intermediate composition of above was applied onto hair and after processing of 10 min and without rinsing off oxidizing composition was applied and immediately afterwards the curlers were taken off from hair and oxidizing composition was processed further for about 10 minutes and rinsed off from hair. Homogeneous wave appearance and natural feeling hair was obtained. Exclusion of the first step resulted in less homogeneous perm appearance and especially natural hair feeling was lost. It was furthermore observed that hair appear and feel less damaged.

EXAMPLE 3

The 3 compositions of Example 1 were used in this example. The permanent shaping was carried out as described in example wherein additionally after rinsing off the reducing agent and before application of the oxidizing agent the first aqueous composition was applied as an intermediate treatment and processed for 5 min and without rinsing off oxidizing composition was applied. The rest of the process was exactly the same as in Example 1. It was observed that pretreatment and intermediate treatment was affected the perming efficiency positively. Perming either without both first step and intermediate treatment or only with intermediate treatment were resulted in much weaker and less preferred results.

EXAMPLE 4

First Aqueous Composition

|  | % by weight |
| --- | --- |
| Coenzyme Q10 | 0.2 |
| Polysorbate-80 | 0.2 |
| Magnesium sulfate | 5 |
| Di amide compound * | 0.2 |
| Cetrimonium chloride | 1.0 |
| Arginine | 0.5 |
| Citric acid | q.s. to pH 4.2 |
| Water | q.s. to 100 |

* Bis (methoxypropylamido) isodocosane which corresponds to compound F among the structures disclosed above.

Alkaline Permanent Wave for Damaged Hair

|  | % by weight |
| --- | --- |
| Ammonium thioglycolate (60%) | 0.9 |
| Cystein hydrochloride | 5.7 |
| Ammonium hydrogen carbonate | 1.5 |
| Acetylcystein | 0.7 |
| Cetrimonium chloride | 0.1 |
| 1,3-butylene gylcol | 0.5 |
| Polyquaternium-39 | 1.5 |
| Amodimethicone | 0.2 |
| Oleic acid | 0.05 |
| Perfume | 0.4 |
| Ammonia, 25% | ad pH 9.8 |
| Water | q.s. 100.0 |

Intermediate Composition

|  | % by weight |
| --- | --- |
| Coenzyme Q10 | 0.2 |
| Polysorbate-80 | 0.2 |
| Magnesium sulfate | 10 |
| Hydrogen peroxide | 2.5 |
| Di amide compound * | 0.2 |
| Cetrimonium chloride | 1.0 |
| Arginine | 0.5 |

-continued

|  | % by weight |
| --- | --- |
| Citric acid | q.s. to pH 4.2 |
| Water | q.s. to 100 |

* Bis (methoxypropylamido) isodocosane which corresponds to compound F among the structures disclosed above.

The permanent wave achieved with the above compositions was similar to the one obtained with the composition according to Example 3. Exclusion of first aqueous composition and/or intermediate treatment led to substantially weaker waves.

EXAMPLE 5

First Aqueous Composition

|  | % by weight |
| --- | --- |
| Coenzyme Q10 | 0.1 |
| Polysorbate-80 | 0.2 |
| Sodium chloride | 10 |
| Hydrogen peroxide | 2.5 |
| Behentrimonium chloride | 0.8 |
| Arginine | 0.5 |
| Citric acid | q.s. to pH 4.2 |
| Water | q.s. to 100 |

Neutral Permanent Wave for Normal Hair

A permanent waving product consisting of two Compositions A and B, filled into a two-chamber packaging the chambers of which were kept separate until application, was prepared by destruction of the separating wall prior to application onto hair.

Composition A:

| Ammonium hydrogen carbonate | 4.5 (g) |
| --- | --- |
| Polyquaternium-6 | 1.0 |
| PEG-65-Hydrogenated castor oil | 0.8 |
| Isopropyl alcohol | 1.5 |
| Ethoxydiglycol | 2.0 |
| Cocoamidopropyl betaine | 1.0 |
| Coenzyme Q10 | 0.2 |
| Perfume | 0.3 |
| Turbidifying agent | 0.5 |
| Ammonia, 25% | ad pH 8.4 |
| Water | q.s. 72.0 |

Composition B:

| Ammonium thioglycolate, 70% | 18.0 (g) |
| --- | --- |
| Thiolactic acid | 2.0 |
| 2-Methyl-1.3-propanediol | 0.5 |
| Ammonia, 25% | ad pH 5.5 |
| Water | q.s. 28.0 |

After admixture of both Compositions a ready-to-use product with a pH-value of 7.4 was obtained.

Intermediate Composition

|  | % by weight |
| --- | --- |
| Coenzyme Q10 | 0.1 |
| Polysorbate-80 | 0.2 |
| Sodium chloride | 10 |
| Hydrogen peroxide | 2.5 |
| Behentrimonium chloride | 0.8 |
| Arginine | 0.5 |
| Citric acid | q.s. to pH 4.2 |
| Water | q.s. to 100 |

With these compositions the hair was permanently waved according to the process of Example 3. Therefore, hair was shampooed and towel dried and first aqueous composition was applied and processed for 5 min and hair was put on curlers and reducing composition given above after mixing the two parts, was applied onto hair and processed for about 20 minutes, rinsed off from hair and intermediate composition of above was applied onto hair and processed for 5 min and without rinsing off oxidizing composition comprising 2.5% by weight hydrogen peroxide and 0.2% Coenzyme Q10 was applied and processed for about 8 minutes and rinsed off from hair. Homogeneous wave appearance and natural feeling hair was obtained. Exclusion of first aqueous composition and intermediate treatment resulted in less homogeneous perm appearance.

EXAMPLE 6

First Aqueous Composition

|  | % by weight |
| --- | --- |
| Coenzyme Q10 | 0.1 |
| PEG-60 Hydrogenated castor oil | 0.2 |
| Sodium chloride | 10 |
| Hydroxyethyl cellulose | 0.2 |
| Cetrimonium chloride | 0.5 |
| Arginine | 0.5 |
| Citric acid/sodium hydroxide | q.s. to pH 6.5 |
| Water | q.s. to 100 |

Neutral Permanent Wave for Dyed Hair

A permanent waving product filled into a two-chamber package was prepared in analogy to Example 4:

Composition A:

| Ammonium hydrogen carbonate | 3.5 (g) |
| --- | --- |
| Polyquaternium-11 | 0.5 |
| Ethanol | 0.5 |
| 1-Methoxypropanol | 1.0 |
| Cocoamidopropyl betaine | 1.0 |
| PEG-25-glyceryl cocoate | 0.8 |
| Coenzyme Q10 | 0.1 |
| Oleic acid | 0.05 |
| Perfume | 0.3 |
| Turbidifying agent | 0.5 |
| Ammonia, 25% | ad pH 8.3 |
| Water | q.s. 72.0 |

Composition B:

| Ammonium thioglycolate, 70% | 13.0 (g) |
| --- | --- |
| Thiolactic acid | 0.5 |
| 2-Methyl-1.3-propanediol | 1.5 |
| Ammonia, 25% | ad pH 5.5 |
| Water | q.s. 28.0 |

A product with a pH-value of 7.4 was obtained by admixture of the Compositions immediately prior to application.

Intermediate Composition

|  | % by weight |
| --- | --- |
| Coenzyme Q10 | 0.1 |
| PEG-60 Hydrogenated castor oil | 0.2 |
| Sodium chloride | 10 |
| Hydrogen peroxide | 2.5 |
| Cetrimonium chloride | 0.5 |
| Arginine | 0.5 |
| Citric acid | q.s. to pH 4.2 |
| Water | q.s. to 100 |

After application onto dyed hair as described in Example 5, this compositions resulted in an expressive permanent wave, which had not effect whatever on the color gloss and color intensity. Exclusion of first aqueous composition and intermediate treatment resulted in loss of effects.

EXAMPLE 7

First Aqueous Composition

| Asparagic acid | 0.25% by weight |
| --- | --- |
| Glutamic acid | 0.50 |
| Alanin DL | 0.25 |
| Behentrimonium chloride | 1.00 |
| Guar gum | 0.25 |
| Potassium iodide | 5.00 |
| Polysorbate-80 | 0.10 |
| Coenzyme Q10 | 0.05 |
| Citric acid/sodium hydroxide | q.s to pH 6.8 |
| Water | q.s. to 100 |

The above composition had a pH of 4.10.

Alkaline Permanent Waving Gel

| Ammonium thioglycolate, 70% | 15.0 (g) |
| --- | --- |
| Ammonium hydrogen carbonate | 4.5 |
| PEG-40-Hydrogenated castor oil | 0.7 |
| $C_{12}$-$C_{18}$-Fatty alcohol mixture | 3.5 |
| Cetrimonium chloride | 2.0 |
| Amodimethicone | 0.05 |
| 2-Methyl-1.3-propanediol | 0.5 |
| Polyquaternium-28 | 0.1 |
| Perfume | 0.3 |
| Ammonia, 25% | ad pH 8.0 |
| Water | q.s. 100.0 |

Intermediate Treatment Composition

| Asparagic acid | 0.25% by weight |
| --- | --- |
| Glutamic acid | 0.50 |
| Alanin DL | 0.25 |
| Behentrimonium chloride | 1.00 |
| Hydrogen peroxide | 1.50 |
| Magnesium sulfate | 10.00 |
| Polysorbate-80 | 0.10 |
| Coenzyme Q10 | 0.05 |
| Water | q.s. to 100 |

The above composition had a pH of 4.10.

The above compositions was applied in the same way as in Example 3 and resulted in expressive waves and natural hair feel.

EXAMPLE 7

Straightening Composition

| Thioglycolic acid | 8.0 (% by wt.) |
| --- | --- |
| $C_{16}$-$C_{22}$-Fatty alcohol mixture | 3.5 |
| Oleth-50 | 2.5 |
| Laureth-23 | 1.5 |
| Polyquaternium-2 | 0.8 |
| Oleic acid | 0.1 |
| Ethanol | 5.0 |
| Perfume | 0.6 |
| Monoethanolamine | ad pH 9.3 |
| Water | q.s. 100.0 |

Intermediate Composition

|  | % by weight |
| --- | --- |
| Coenzyme Q10 | 0.1 |
| Poysorbate-80 | 0.1 |
| Sodium chloride | 10 |
| Hydrogen peroxide | 2.5 |
| Cetrimonium chloride | 0.8 |
| Arginine | 0.5 |
| Citric acid | q.s. to pH 4.2 |
| Water | q.s. to 100 |

Kinky hair was straightened according to process wherein hair was shampooed and first aqueous composition of example 1 was applied onto hair and after processing of 10 min at ambient temperature, the above reducing composition was applied onto hair and processed from 20 min at ambient temperature and rinsed off from hair and hair was towel dried and treated with the above intermediate composition and without rinsing off hair was dried. Subsequently hair was straightened with a hot iron having flat shape and a temperature of approximately 140° C. and afterwards treated with an oxidizing composition comprising 2% by weight of hydrogen peroxide at pH 3. Finally hair was rinsed off and dried with a drier. Hair was excellently straightened and felt natural and soft upon touching. Exclusion of first aqueous composition and intermediate treatment resulted in loss of effects.

The invention claimed is:

1. A process for permanent shaping hair wherein hair is washed and/or shampooed and an aqueous composition comprising at least one inorganic salt was applied onto hair in the first step wherein aqueous composition comprising inorganic salt applied in the first step also comprises at least one thickening agent, at least one surfactant, at least one conditioning agent and at least one solvent and processed up to 20 min and rinsed off, and subsequently a composition comprising at least one reducing agent is applied onto hair and after processing of 1 to 30 min at a temperature of 20 to 45° C. rinsed off from hair and a composition comprising at least one oxidizing agent is applied and rinsed off from hair after a processing time of 1 to 30 min and at a temperature of 20 to 45° C. wherein hair is put on curlers prior to application of a composition comprising reducing agent and wherein an aqueous composition comprising at least one inorganic salt is additionally applied onto hair after rinsing of the reducing composition and prior to application of the oxidizing composition, which comprises at least one oxidizing agent.

2. The process according to claim 1, wherein curlers were removed from hair after application of the oxidizing agent or at the end of the processing time of oxidizing agent.

3. The process according to claim 1, wherein aqueous composition comprises at least one inorganic salt at a concentration of 0.01 to 20% by weight calculated to total of the composition.

4. The process according to claim 1, wherein at least one inorganic salt is selected from salts of mono or divalent cations with mono and divalent anions.

5. The process according to claim 4, wherein at least one inorganic salt is selected from sodium chloride, sodium sulfate, magnesium sulfate, potassium chloride, potassium sulfate, magnesium chloride, calcium chloride, ammonium chloride, ammonium sulfate, sodium iodide, potassium iodide, copper chloride, cupper sulphate, cobalt chloride, cerium sulphate, cerium chloride, vanadium sulphate, lithium chloride, potassium dichromate, magnesium acetate, calcium nitrate, barium nitrate, magnesium oxide, and ammonium nitrate.

6. The process according to claim 4, wherein at least one inorganic salt is selected from magnesium sulfate, sodium chloride and potassium iodide.

7. The process according to claim 1, wherein reducing composition comprises at least one reducing agent at a concentration of 0.5 to 15% by weight calculated to total of the composition and selected from thioglycolic acid, thiolactic acid, ammonium salt of thioglycolic acid, ethanolamine salt of thioglycolic acid, ammonium salt of thiolactic acid, ethanolamine salt of thiolactic acid, cysteine, cysteine hydrochloride, homocysteine, cysteamine, N-acetyl cysteine, thioglycerol, ethanediol monothioglycolate, 1,2-propyleneglycol monothioglycolate, isomer mixture of 1,2-propyleneglycol monothioglycolate, 1,3-propanediol monothioglycolate, isomer mixture of 1,3-propanediol monothioglycolate, 1,3-butanediol, isomer mixture of 1,3-butanediol, 1,4-butanediol monothioglycolate, isomer mixture of 1,4-butanediol monothioglycolate, diethyleneglycol monothioglycolate, triethyleneglycol monothioglycolate, tetraethyleneglycol monothioglycolates, glycerol monothiolactate thio acids thio esters thereof, mixtures thereof.

8. The process according to claim 1, wherein any of the compositions comprise one or more of the compounds selected from a—ubichinones of the formula

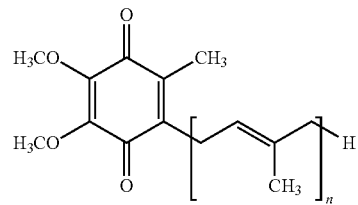

where n is a number between 1 and 10, b—amino acid at a concentration of 0.01 to 10%, c—ceramide of compound with the general formula

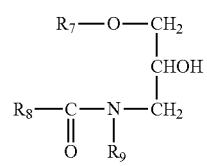

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6, a—sterol, especially phytosterol, b—fatty acid, c—diamide compounds are according to the general structure

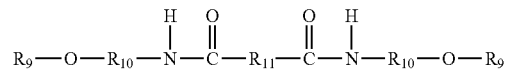

wherein $R_9$ is a linear or branched, saturated or unsaturated alkyl chain with 1 to 12 C atoms which may be substituted with hydroxy and/or alkoxy groups, $R_{10}$ is linear or branched alkyl chain with 1 to 5 C atoms, d—silicone compound, and e—natural oil.

* * * * *